US005702722A

United States Patent [19]

Tournier et al.

[11] Patent Number: 5,702,722

[45] Date of Patent: Dec. 30, 1997

[54] LIPOSOMES WITH ENHANCED ENTRAPMENT CAPACITY, METHOD AND USE

[75] Inventors: Hervé Tournier, Valleiry, France; Michel Schneider, Troinex, Switzerland; Christian Guillot, Le Chable-Beaumont, France

[73] Assignee: Bracco Research S.A., Carouge, Sweden

[21] Appl. No.: 527,087

[22] Filed: Sep. 12, 1995

[30] Foreign Application Priority Data

Sep. 30, 1994 [EP] European Pat. Off. .............. 94810570

[51] Int. Cl.[6] .............................................. A61K 9/127

[52] U.S. Cl. ............................ 424/450; 264/4.1; 264/4.3; 264/4.6; 428/402.2

[58] Field of Search ............................ 424/450; 264/4.1, 264/4.3, 4.6; 428/402.2

[56] References Cited

U.S. PATENT DOCUMENTS

| | | | |
|---|---|---|---|
| 4,162,282 | 7/1979 | Fulwyler | 264/9 |
| 4,485,054 | 11/1984 | Mezei | 264/4.6 |
| 4,508,703 | 4/1985 | Redzinak et al. | 424/38 |
| 4,619,795 | 10/1986 | Cohen | 264/4.6 |
| 4,622,188 | 11/1986 | Adamich | 264/4.6 |

FOREIGN PATENT DOCUMENTS

| | | |
|---|---|---|
| 0 087 993 | 9/1983 | European Pat. Off. . |
| 0 119 020 | 9/1984 | European Pat. Off. . |
| 0 186 352 | 7/1986 | European Pat. Off. . |
| 33 35 701A1 | 4/1984 | Germany . |
| 6246150 | 9/1994 | Japan . |

OTHER PUBLICATIONS

J. Fibe U. M. Regitz 'Römpp–Chemie–Leikon, 9th Edition, vol. 3' 1990, Georg Thieme Verlag Stuttgart (DE) pp. 1860–1861 "HPLC".

*Primary Examiner*—Gollamudi S. Kishore

*Attorney, Agent, or Firm*—Nixon & Vanderhye P.C.

[57] ABSTRACT

The invention relates to a dry deposit as a precursor to liposome vesicles, the precursor being a three dimensional expanded structure with bulk density between 0.01 and 0.001 g/cm$^3$. The invention also concerns a method of making liposome vesicles with an enhanced entrapment capacity by dissolving one or more film forming lipids in at least one organic solvent to form a solution in a reaction vessel, evaporating the solvent to form an expanded three dimensional porous lipid structure, contacting the lipid deposit with an aqueous carrier phase, and producing liposome vesicles entrapping the carrier phase as well as an apparatus comprising an array of tubing or an inert packing which serves as a material support or a matrix surface for the deposition of lipids produced according to the method.

19 Claims, 4 Drawing Sheets

LIPOSOMES WITH ENHANCED ENTRAPMENT CAPACITY, METHOD AND USE

TECHNICAL FIELD

The invention relates to a liposome vesicle precursor in the form of a dry lipid deposit and a method of making liposome vesicles with enhanced entrapment capacity by dissolving one or more film forming lipids in at least one organic solvent in a reaction vessel, depositing the lipids by evaporation of the solvent, contacting the lipid deposit with an aqueous solution carrier phase, and producing liposome vesicles entrapping the solution. The invention also concerns a an apparatus for carrying out the method, contrast agents comprising the liposome vesicle precursor and a method of making contrast agents using the precursor.

BACKGROUND ART

Liposomes vesicles whose binding envelope consists of bi- or multilayer of lipid molecules have been long recognised as drug delivery systems which can improve therapeutic and diagnostic effectiveness of many drugs and contrast agents. Experiments with a number of different antibiotics and X-ray contrast agents have shown that better therapeutic activity or better contrast with a higher level of safety may be achieved by encapsulating drugs and contrast agents with liposomes. Great interest in liposomes as encapsulating systems for drugs has revealed that a successful development and commercialisation of such products requires reproducible methods of large scale production of lipid vesicles with suitable characteristics. Consequently, a search for methods which will consistently produce liposome vesicles of the required size and concentration, size distribution and entrapping capacity regardless of the nature of lipid mixture have been initiated. Such methods ought to provide liposomes with consistent active substance to lipid ratio while respecting currently accepted good manufacturing practices. As a result of the search, and due to the fact that the liposome behaviour can vary substantially with various production parameters, many different methods of manufacture have been proposed so far.

Conventional liposome preparation methods include a number of steps in which multi- or the bilayer-forming components (phospholipids or mixtures of phospholipids with other lipids e.g. cholesterol) are dissolved in a volatile organic solvent or solvent mixture in a round bottom flask followed by evaporation of the solvent under conditions (temperature and pressure) which will prevent phase separation. Upon solvent removal a dry lipid mixture, usually in form of a film deposit on the walls of the reactor, is hydrated with an aqueous medium which may contain dissolved buffers, salts, conditioning agents and an active substance to be entrappeal. Liposomes will form in the hydration step whereby a proportion of the aqueous medium becomes encapsulated in the liposomes. The hydration can be performed with or without energising the solution by means of stirring, sonication or microfluidisation with subsequent extrusion through one or more polycarbonate filters. The free non-encapsulated active substance can be separated for recovery and the product is filtered, sterilised, optionally lyophilised, and packed.

Hydration, more than any other step, influences the type of liposomes formed (size, number of lipid layers, entrapped volume). The nature of fie dried lipid, its surface area, and its porosity are of particular importance. Thus it has been established that the hydration and entrapping process are most efficient when the film of dry lipids is kept thin. This means that greater the lipid quantity, greater the surface for deposition of the lipids is required, it also means that even though glass beads and other inert insoluble particles are used to increase the surface area available for film deposition, the thin film method remains largely a laboratory method.

Other methods of making liposomes involving injection of an organic solutions of lipids into an aqueous medium with continuous removal of solvent, use of spray drying, lyophilization, microemulsification and microfluidization, etc. have been proposed a number of publications or patents such as for example U.S. Pat. No. 4,529,561, U.S. Pat. No. 4,572,425, etc.

An attempt to solve problems of the scale-up of liposome production has been described in the U.S. Pat. No. 4,935,171 (Vestar). There is disclosed a method for preparing liposomes in commercial quantities by forming a homogeneous and uniform lipid film in a thin-film evaporator through evaporation of the organic solvent. After drying of the thin lipid film which is formed on the inner wall of the evaporator, the deposit is in situ hydrated with an aqueous phase under agitation provided by the rotor. Although the solution proposed in this document seems to be a step in the right direction the lipid film surface to the reactor volume ratio is only slightly, if not marginally, better than that of the round-bottom flasks used on laboratory scale. The reactor's space time yield or productivity is still far too low for the process to be economically sound and competitive.

Different aspects of the liposome manufacturing have been addressed and a number of improvements and different solutions to the problem of scale-up have been proposed. Documents such as for example WO-A-86/00238, WO-A-87/00043, U.S. Pat. No. 4,737,323, U.S. Pat. No. 4,753,788, and U.S. Pat. No. 4,781,871 have suggested use of rapid freezing of previously prepared multi lamellar vesicles with subsequent freeze and thaw treatment to improve their entrapment capacity, use of extrusion technique of multilamellar liposomes to improve their size distribution, etc.

So far there has been no suggestion rewards a large scale industrial method whose control of production parameters will allow reproducible process in which large volumes of liquid will be processed within a relatively small reactor space. All known processes of pilot or industrial scale would, typically, be linked to small batches in which processing of large volumes of dilute liposome solutions would require a lot of floor and reactor space as well as handling of large volumes of solutions and solvents. In reality due to relatively low space time yields or productivity of reactors these methods are too cumbersome and far too costly for a large scale commercial production.

SUMMARY OF THE INVENTION

Briefly summarised the invention relates to a supported or unsupported liposome vesicle precursor in the from of a three dimensional structure of expanded lipids with bulk density below 0.1 g/cm$^3$ preferably below 0.08, more preferably between 0.05 and 0.001 and even more preferably between 0.02 and 0.01. By supported structure it is meant that the lipid porous deposit is formed on an array or network of inert supporting material. The lipids forming the deposit are selected from synthetic or natural, saturated and unsaturated phospholipids including phosphatidic acid, phosphatidyl choline, phosphatidylethanol amine, phosphatidyl serine, phosphatidyl glycerol, phosphatidyl inositol and mixtures thereof. The lipids may further contain substances selected from dicetylphosphate, cholesterol, ergosterol, phytosterol, sitosterol, lanosterol, α-tocopherol, stearic acid, stearyl amine and mixtures thereof.

The invention also concerns a method of making liposome vesicles with enhanced entrapment capacity by dissolving one or more film forming lipids in at least one organic solvent to form a solution. The solution of lipids is introduced into a suitable reaction vessel and subjected to evaporation whereby the drying lipids form expanded three dimensional porous structure whose bulk density is below 0.1 $g/cm^3$, preferably below 0.08, more preferably between 0.05 and 0.001 and even more preferably between 0.02 and 0.01. Thereafter, the porous structure is contacted with an aqueous carrier phase to produce liposome vesicles entrapping a portion of the carrier phase.

The invention further comprises an apparatus for the manufacture of liposomes with high entrapment capacity according to the above method comprising a reaction vessel with an inlet and an outlet, a connection to a vacuum, means for cooling or heating, a control means, and a packing comprising an array of a closely packed tubing of an inert material. Preferably, the tubing is stainless steel tubing with the inner diameter of between 0.5 mm and 5 mm and the wall thickness of between 0.5 mm and 2 mm. Alternatively, the packing, which may be stationary or moving e.g. fluidized, may comprise Raschig rings, hollow glass spheres, reticulated carbon, reticulated vitreous carbon, reticulated metal, glass or metal wool and glass or metal fibre.

The three dimensional lipid structures of the invention are very suitable for a large scale manufacture of liposomes with high entrapment capacity.

When incubated with an aqueous carrier phase containing a contrast medium, the three dimensional lipid structures of the invention are particularly suitable for the manufacture of diagnostic contrast agents.

DETAILED DESCRIPTION OF THE INVENTION

Figure 1A:
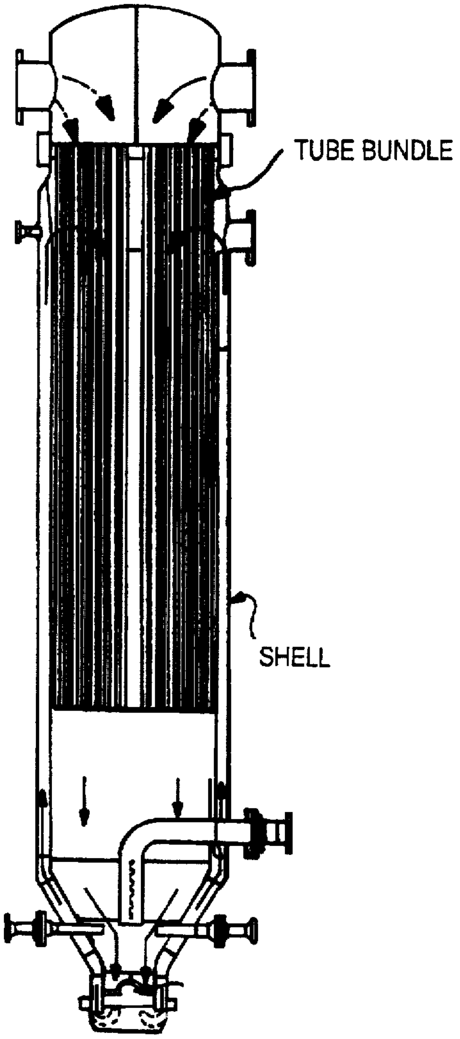
FIG. 1 is a schematic diagram of the reactor with a cut-out showing the expanded three dimensional lipid structure of the invention.
Figure 1B:
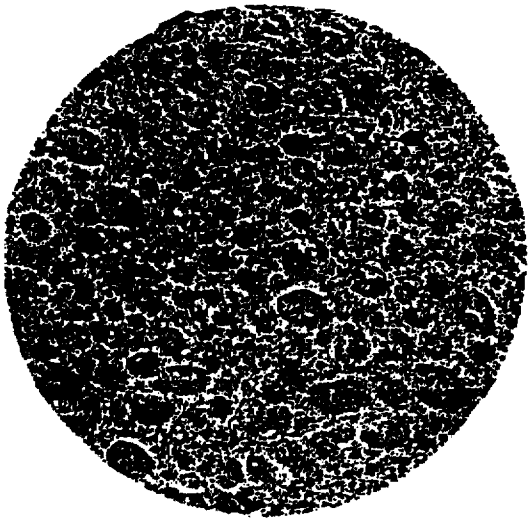
Figure 2:
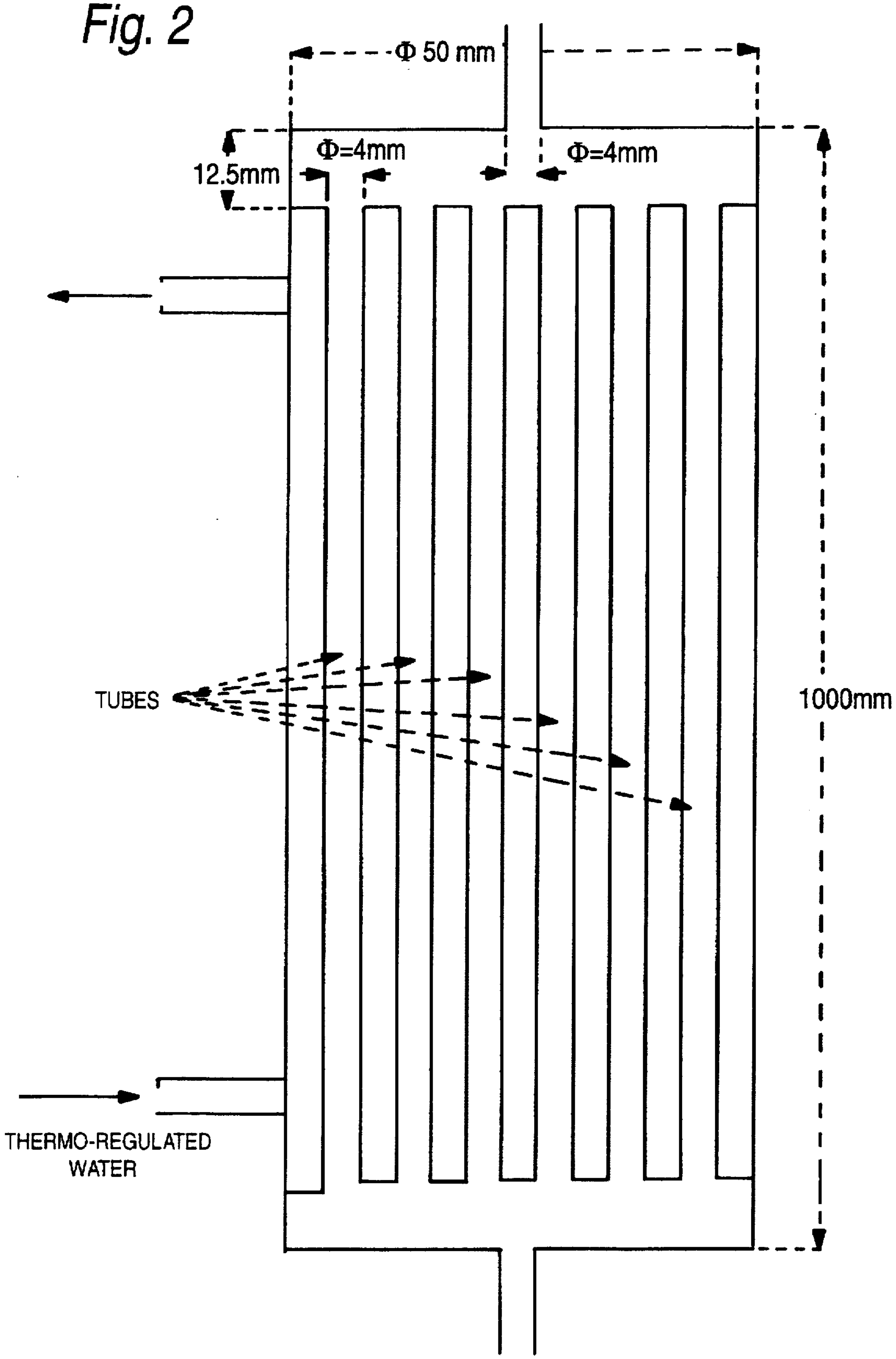
FIG. 2 is a schematic diagram of the reactor with an array of an inert tubing.

This invention is based on the unexpected finding that optimal liposome formation and enhanced reactor capacity are obtained if during the production of the vesicles, the lipid deposit obtained by evaporation of the solvent from an organic solution of one or more film forming lipids in at least one organic solvent, prior to contacting with an aqueous carrier phase, is expanded into a three dimensional structure whose bulk density is below 0.1 $g/cm^3$, preferably below 0.08, more preferably between 0.05 and 0.001 and even more preferably between 0.02 and 0.01. Although the exact reasons for such unexpected results have not been thoroughly established, it is assumed that the method provides an exceptionally large surface to volume ratio of the deposit whose subsequent hydration is therefore more efficient. High yields of liposomes of the desired size and distribution are thus produced by the method which is particularly easy to scale up and control. Having a large surface to volume ratio the expanded lipid structures improve the space time yield of reactors, whereby the technique becomes industrially very attractive. In addition, to ease scale-up and promote high productivity, the method provides further advantages which include faster reactor turn around time, ease of control of the hydration step, reduced processing times, use of inexpensive materials, and finally use of the same reactor for deposition, solvent evaporation, hydration of the expanded lipid structure and sterilization of the liposome vesicles formed.

It has been established that the porous structures of pure lipids of the invention have very large surface to volume ratio. Unfortunately, due to the great fragility of the expanded structure the exact surface area of the unit of volume or weight of the expanded lipid structure could not have been established with great accuracy. However, a conservative estimate of the total surface area of 1 g of the expanded structure of the invention suggests that the total surface area may vary between 0.1 and 50 $m^2$ which implies surface to volume ratios of between 10 to $0.5\times10^5$.

The expanded three dimensional lipid structure may be obtained through evaporation of the organic solvent from a reaction vessel which contains an inert porous network or a support which serves as a material support or a matrix surface for the deposition of lipids. The inert network may be any convenient material with a relatively large surface to volume ratio and it may include an array of tubing or an array of inert packing such as hollow glass spheres, reticulated carbon, reticulated vitreous carbon, reticulated metal, glass, ceramic or metal wool and glass, ceramic or metal fibre. When an array of tubing is used the tubing dimensions should be chosen such that maximal ratio of surface to volume is achieved. The experiments carried out in the course of the development and characterisation of the reactor according to the invention have shown that in a given configuration the tubing with an inner diameter of between 0.5 mm and 5 mm and wall thickness between 0.5 and 2 mm has provided favourable results, however, another configuration of the reactor may favour other tubing dimensions. It has been established that since the lipid solution is spread over the inner and outer surface of the tubing by gravity an array of vertically arranged tubing is preferred although a helical arrangement is also possible.

In order to facilitate uniform deposition of the lipid films the inert packing may be gently fluidized or the reactor packed with Raschig rings or any other inert material such as that mentioned above may be fed with the lipid solution from the top and left to gently trickle down the packing. It is believed that excellent results obtained in the trickle tower arrangement come from the fact that an efficient control of deposit thickness is achieved by the trickle fashion of contacting of the lipid solution and the support. The excess liquid being constantly removed whereby uniform liquid thickness on the whole surface of the support is ensured. To further assist uniform formation of the coating of the lipid solution on the packing air or an inert gas such as nitrogen may be introduced in counter-current fashion for a period of time. The gas is usually cold however, under certain conditions it may be desirable that the temperature of the gas is chosen such that drying and expansion of the lipid film is assisted or performed using a hot gas.

After drying and expansion of the deposit consisting of pure or lipids with usual degree of purity into the three dimensional structure, the deposit is contacted with an aqueous carrier phase. Depending on the configuration of the reactor the carrier phase may be introduced at the lower end of the reactor e.g. in the case of trickle tower or fluidized bed configuration or at the top of the reactor column (in case of the fixed array of tubing). The aqueous carrier phase used may be pure or it may contain biologically active substances, contrast agents or both. Virtually any biologically active substance can be entrapped in the liposomes produced according to the invention. Such substances include but are not limited to antibacterial compounds such as gentamycin, antiviral compounds such as rifamycins, antifungal compounds such as amphotericin B, antiparasitic compounds such as derivatives of antimony, antineoplastic compounds such as mitomycin C, doxorubicin and cisplatinum, proteins such as albumin and lipo-proteins, immunoglobulines, toxins such as diphteria toxin, enzymes such as catalase, hormones, neurotransmitters, radio-opaque compounds such as $^{99}$Tc, fluorescent compounds such as carboxy fluoroscein, anti-inflammatories such as salicylic acid and ibuprofen, anesthetics such as dibucaine or lidocaine, etc.

Very good results and high entrapment loadings are achieved with iodinated X-ray contrast agents such as iopamidol, iomeprol, iohexol, iopentol, iotrolan, iodixanol, ioglucol, etc. The iodine to lipid ratio of the liposome vesicles according to the invention is at least 2.75.

The evaporation of the organic solvent or the mixture of solvents is carried out at above ambient temperatures or reduced pressure or both. Experiments have shown that the rate of evaporation has a strong influence on the degree of expansion of the lipid structure. Hence for optimal expansion, one will appropriately control the amount of heat and the pressure within the reactor. The control becomes particularly important near the end of solvent evaporation, i.e. when the solution thickens and becomes viscous. At this point, a slight reduction of pressure will result in a relatively fast expansion (foaming). It has been established that by balancing the temperature and pressure for a given solvent or solvent mixture different degrees of expansion of the lipid deposit may be achieved. Best results are obtained when the organic solvent is selected from petroleum ether, chloroform, methanol, ethanol, propanol, isopropanol, n-butanol, tert-butanol, pentanol, hexanol, pentane, hexane, heptane, cyclohexane and mixtures thereof. Preferably the solvent is an azeotropic mixture of two solvents. Good results have been obtained with azeotropic mixtures of ethanol with cyclohexane, chloroform with methanol and iso-propanol with hexane.

Lipids used for production of liposome vesicles are conventional and are selected from synthetic or natural, saturated and/or unsaturated phospholipids including phosphatidylcholine, phosphatidylethanolamine, phosphatidylserine, phosphatidylglycerol, phosphatidylinositol and phosphatidic acid. The following phospholipids are particularly useful dipalmitoylphosphatidyl choline, dipalmitoylphosphatidyl glycerol, dipalmitoylphosphatidyl acid, dipalmitoylphosphatidyl ethanolamine and the corresponding distearoyl- and dimyristyl- counterparts and mixtures thereof. Those lipids or their mixtures may further contain substances selected from dicetylphosphate, cholesterol, ergosterol, phytosterol, sitosterol, lanosterol, α-tocopherol, stearic acid, stearyl amine and mixtures thereof.

The invention also includes a supported or unsupported three dimensional structure of expanded dry lipids with density of below 0.1 g/cm$^3$, preferably below 0.08 g/cm$^3$ and more preferably with the density of between 0.05 and 0.01 g/cm$^3$. By supported structure it is meant that the lipid porous deposit is formed on an array of inert supporting material.

The expanded three dimensional lipid structures are extremely useful for the manufacture of liposomes with high entrapment capacity particularly when these liposomes are used to carry drugs or diagnostic contrast agents. In such a case the porous three dimensional lipid structure is contacted with an aqueous solution containing the drug or the diagnostic agent as an active ingredient whereby liposomes will form and encapsulate the ingredient. The liposomes carrying the active substance are then processed as appropriate in a conventional way. Alternatively, a suspension of "empty" liposome vesicles i.e. liposome vesicles containing only aqueous liquid carrier may be formed first. In the subsequent step these "empty" liposomes are contacted with a solution containing an active ingredient and the vesicles loaded using for example trans-membrane loading technique.

The invention further comprises an apparatus for the manufacture of liposomes with high entrapment capacity comprising a reaction vessel with an inlet and an outlet, a connection to a vacuum, means for cooling or heating, a control means, and a packing, characterised in that the packing is an array of a closely packed tubing of an inert material. The tubing having the inner diameter of between 0.5 mm and 5 mm and the wall thickness of between 0.5 and 2 mm is preferably arranged in a vertical fashion although a coil-like arrangement is also possible.

The following examples further illustrate the invention:

EXAMPLE 1

Reactor Characterisation

A vertical, thermoregulated, 1 meter high, 316 L stainless steel column with inner diameter of 50 mm fitted at its bottom end with a metal grid was filled with 12 stainless steel tubes. The inner diameter of the tubing was 4 mm and wall thickness of 1 mm. Prior to insertion into the reactor the tubing was spot welded to form an array of parallel tubes. The same reactor configuration but with tubing of 2 mm and 3 mm diameter have also been prepared and tested.

Prior to the tests directed to expansion of the lipid deposits characterisation of the reactor was carried out by deposition of non-expanded lipid films using the following lipid composition:hydrogenated soy lecithin/dicetylphosphate in 9:1 molar ratio. Experiments were performed to determine the best conditions for the deposition of the lipids in the tubes and to establish the impact of the lipid concentration, internal diameter and nature of the tubes and rate of drainage of the lipid solution. In all cases, the lipid solutions in chloroform were introduced into the tubes at room temperature and after filling of the tubes from the bottom the lipid solutions were drained at a controlled rate. The deposit was dried at 80° C. under nitrogen by evaporation of the solvent and the dry deposit rinsed 3 times with a small amount of chloroform.

TABLE 1

| Lipid conc. | Lipids deposited in mg of lipid/100 cm$^2$ | |
|---|---|---|
| g/l | 3 mm tube | 4 mm tube |
| 180 | 33.1 | 23.3 |
| 220 | 43.7 | 29.7 |
| 260 | 62.5 | 40.0 |
| 300 | 81.5 | 56.5 |
| 320 | 94.5 | 80.4 |
| 340 | 111.3 | 84.2 |

Figure 3:
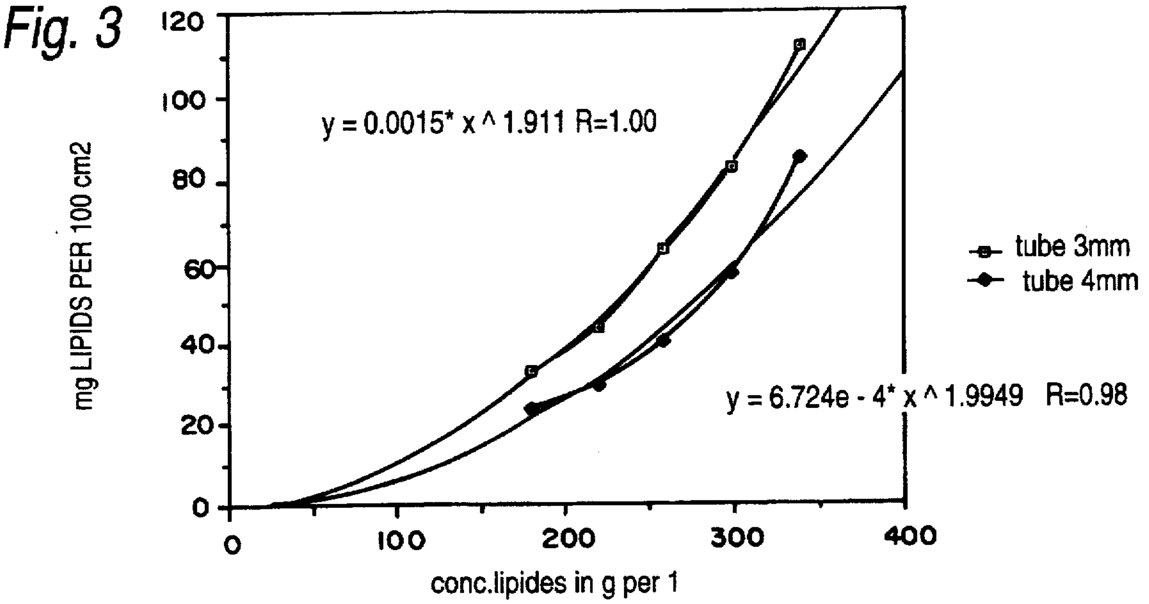
FIG. 3 is a plot of lipid deposition vs concentration.

As shown in Table 1 and FIG. 3 the amounts of lipids deposited at various lipid concentrations and two different diameters of stainless steel tubing the lipid coating increases with an increase of the lipid concentration. In addition, thicker deposits per unit area are obtained in the 3 mm tubing than in 4 mm. In both cases the amounts of lipids deposited appear to be proportional to the square of the lipid concentration.

Figure 4:
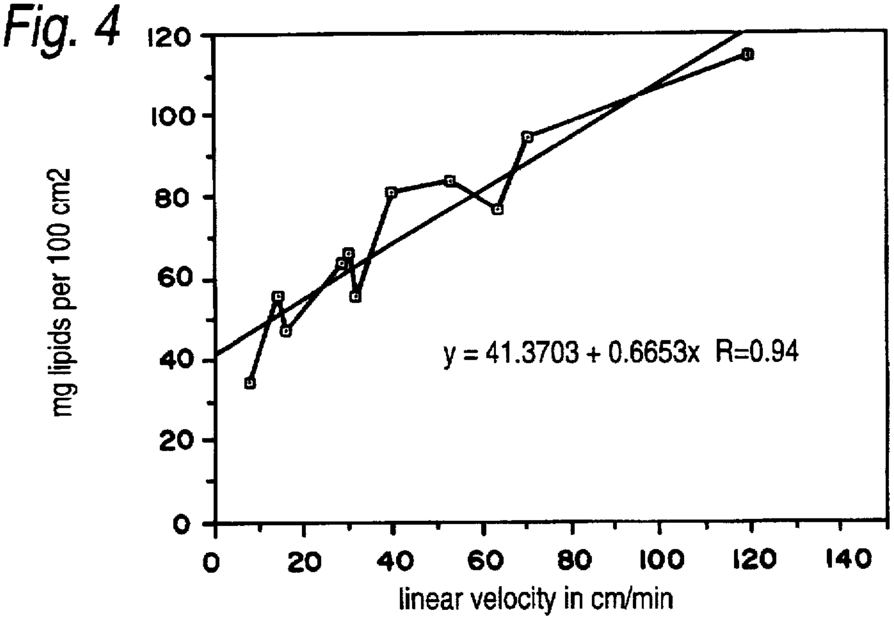
FIG. 4 is a plot of lipid deposition vs linear velocity.

As it can be seen from Table 2, the amount of lipids deposited increases with the race of drainage. However, if these results are expressed as a function of the drainage velocity (in cm per min) rather than drainage flow rate (in ml per min) amounts of the lipids deposited appear to be nearly proportional to the linear velocity. That independently of the actual tube size. See FIG. 4.

TABLE 2

| Drainage rate | Lipids deposited in mg lipid/100 cm² in a tube of | | |
|---|---|---|---|
| ml/min | 2 mm | 3 mm | 4 mm |
| 1 | 55.2 | 55.3 | 37.4 |
| 2 | 76.5 | 63.0 | 47.3 |
| 3.75 | 114.9 | 83.7 | 65.4 |
| 5 | 121.0 | 94.5 | 80.4 |

Additional experiments were carried out in the identical set up but using glass tubes instead of stainless steel ones have shown that there are no major differences between the two supports with regard the lipid deposition. The homogeneity of the lipid coating was determined by cutting the coated steel tubes from the top in 10 cm intervals and measuring the film thickness. The results obtained are given in Table 3.

TABLE 3

| Fraction | Lipids deposited in mg | |
|---|---|---|
| | 3 mm tube | 4 mm tube |
| 1 | 5.15 | 5.13 |
| 2 | 6.63 | 3.77 |
| 3 | 7.22 | 4.52 |
| 4 | 8.20 | 3.50 |
| 5 | 7.59 | 5.58 |
| 6 | 6.55 | 6.16 |
| 7 | 5.59 | 6.38 |
| 8 | 5.63 | 6.21 |
| 9 | 5.22 | 6.97 |
| 10 | 9.06 | 6.86 |
| Mean ± S.D. | 6.68 ± 1.33 | 5.51 ± 1.24 |

Calculation of apparent (bulk) densities of the lipid deposits obtained in the three different reactor configurations have shown that for 2 mm tubing bulk densities were between 0.04 and 0.06 g/cm$^3$, for 3 mm tubing between 0.02 and 0.04 g/cm$^3$ and for 4 mm tubing the bulk densities were between 0.01 and 0.03 g/cm$^3$.

Liposome Production

Figure 5:
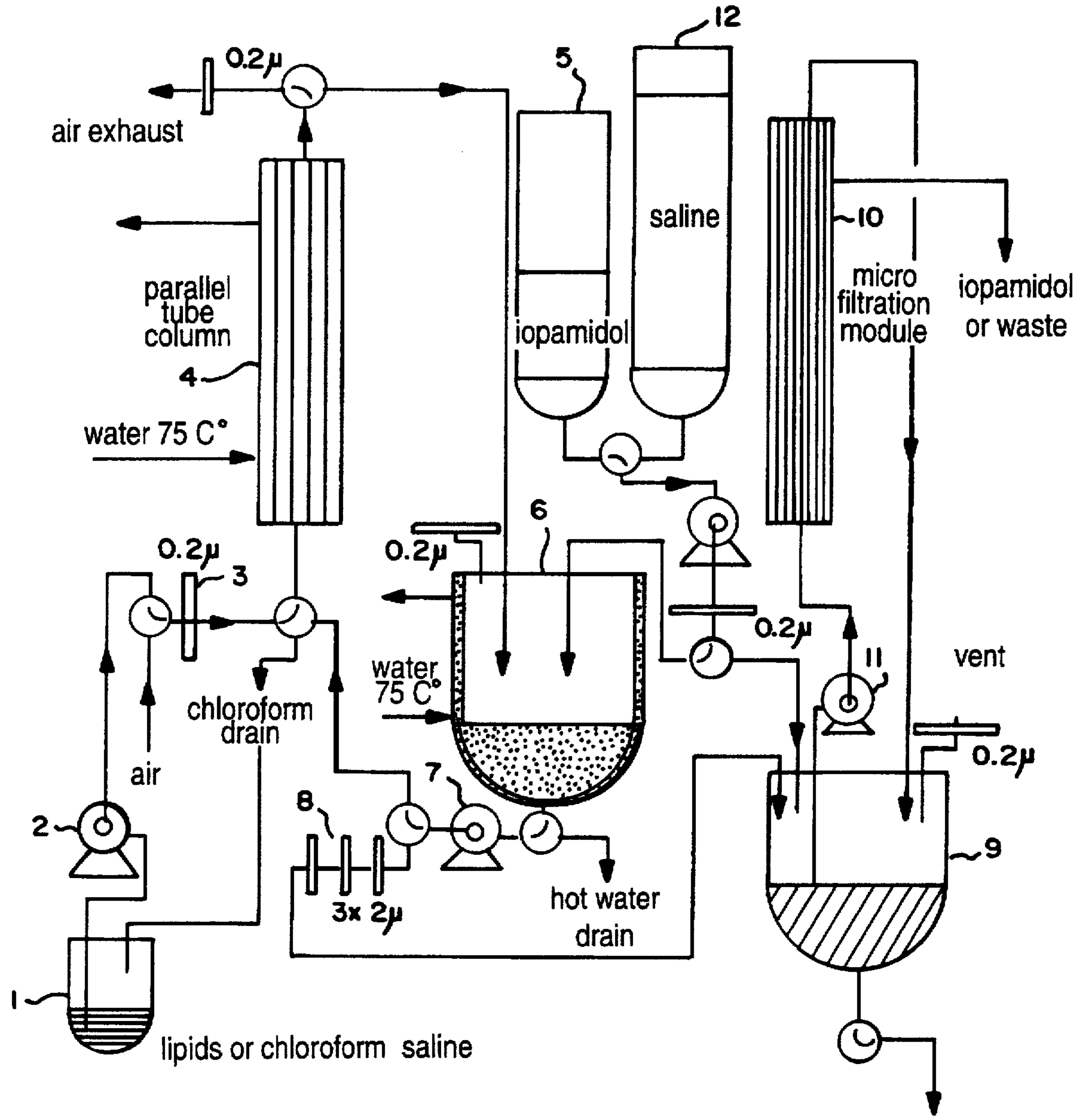
FIG. 5 is a flow chart of the production of a contrast medium using the expanded lipid structures of the invention.

After the characterisation, a new reactor with 250 stainless steel tubes was made and connected into the circuit shown in FIG. 5. 26 g of hydrogenated soy phosphatidylcholine (Nattermann) with 2 g of dicetylphosphate and 106 g of chloroform were placed into 1 liter glass reactor equipped with stirrer, heating jacket, and condenser (1) and heated to 60° C. under stirring until complete dissolution. The lipid solution filtered through the sterile filter (3) and loaded into 316 L stainless steel column with a heating jacket filled with 250 of parallel 1 m long 304 stainless steel tubes (4) by means of the peristaltic pump (2). The excess of solution was removed, the solvent evaporated and the lipids deposited at 80° C. by circulating air from the bottom of the column.

The 2 liter glass reactor with stirrer, heating jacket, condenser (5) was filled with 849 g of iopamidol, 1196 g of water, 0.54 g of EDTA and 1.60 g of Tris and heated at 90° C. under stirring until complete solubilization was obtained. The iopamidol solution was then filtered, transferred to the glass reactor (6) and therefrom to the column (4). The solution was circulated at 75° C. between the reactor (6) and the column (4) by means of the gear pump (7). The liposome suspension formed was then extruded through the filter (8), recovered in the reactor (9) and then concentrated using the microfiltration system (10) by means of pump (11). The concentrated solution was washed with saline (12) to eliminate free iopamidol (diafiltration). Typical iodine to lipid ratios (I/L) for a number of experiments run under different experimental condition were in the range 2.5–3.5 with lipid concentrations between 25 and 35 mg/ml with the liposome mean size of 570 mm.

The production unit can be sterilised (e.g. steam) and is envisaged as a closed-circuit aseptic large scale production unit.

EXAMPLE 2

The Example 1 was repeated in the experimental set-up shown in FIG. 5 but size was scaled-up by a factor four. 518.6 g of hydrogenated soy phosphotidylcholine (Nattermann) with 41.4 g of dicetylphosphate and chloroform 2130.0 g were placed into 3 liter glass reactor equipped with stirrer, heating jacket, and condenser (1) and heated to 60° C. under stirring until complete dissolution. The lipid solution was filtered on the 0.22 μm sterile filter (3) using the peristaltic pump (2). The lipid solution is then transfered into the 316 L stainless steel column with a heating jacket filled with 1000 of parallel 1 m long 304 stainless steel tubes (4) and the excess of the lipid solution removed. The chloroform was evaporated and the lipids dry deposited at 80° C. by circulating air from the bottom of the column.

The 7 liter stainless steel (316 L) reactor with stirrer, heating jacket, condenser (5) was loaded with 2920 g of iopamidol, 4110 g of water, 1.87 g of EDTA and 5.50 g of Tris (HCl qsp for pH 7.2) and heated at 90° C. under stirring until complete solubilization was obtained. The iopamidol solution was then passed through the sterile filter (not shown), transferred to column (4) using the gear pump (7) and circulated at 75° C. between the reactor (6) and the column (4) for a while. The liposome suspension formed was recovered in the reactor (6), extruded through the filter (8) at 75° C. and the liposomes recovered in reactor (9). The liposome solution was then concentrated using the microfiltration system (10). Typical iodine to lipid ratios (I/L) for a number of experiments run under different experimental condition were in the range 2.5–3.5 with lipid concentrations between 25 and 35 mg/ml with the liposome mean size of 570 mm. Bulk density of the lipid deposit varied as a function of the experimental conditions and was estimated to be between 0.08 and 0.05 g/cm$^3$. However the best liposomes were prepared with the bulk densities between 0.01 and 0.02 g/cm$^3$.

EXAMPLE 3

The Example 2 was repeated using as solvent the azeotropic mixture of chloroform and methanol (87/13=v/v). After evaporation of the solvent under reduced pressure 60° C. warm distilled water was added to the reactor. The temperature of the water added was above the transition temperature (54° C.) of the lipids used. The expanded three dimensional lipids deposit obtained was allowed to hydrate and the liposomes formed were distributed homogeneously through the liquid. Liposomes of the MLV type were formed in high yield. After about 1 hour, the liposome suspension containing 5 mg/ml of lipids was extruded at 60° C. through a 2 μm polycarbonate membrane (Nuclepore) and, after cooling to room temperature, it was concentrated to 30 mg/ml by microfiltration using a 0.22 μm micro filter system Prostak (Millipore).

To the concentrated liposome suspension, there was added 1 liter of an aqueous solution containing 1040 g of (S)-N,N'-bis [2-hydroxy-1-(hydroxymethyl)-ethyl]-2,4,6-triiodo-5-lactamido-isophtalamide (iopamidol) i.e. 520 g/l of covalent iodine at 60° C. The resulting mixture (2 l) with iodine concentration of 260 g/l was incubated for about 30 min at 60° C., after which time the iodine concentration outside and inside the liposome core had equalized. The resulting preparation was concentrated to 30 g lipids/l. The entrapped iodine to lipid ratio (I/L) was about 4.0.

EXAMPLE 4

A glass column (500 mm high and 50 mm in diameter) was filled with Raschig rings and operated as a trickle tower reactor. A lipid solution containing 50 g/l of a mixture of distearoylphosphatidyl choline (DSPC), cholesterol and dicetylphosphate with molar ratio 5:4:1 in chloroform was trickled down the column fitted with 35 layers of Raschig rings spread over a nickel mesh as a support until the last layer at the bottom was thoroughly soaked with the solution. The excess of the solution was removed and a stream of hot (80° C.) nitrogen blown from the bottom up through the reactor. The lipid deposit was dried for 2 hours. The nitrogen flow stopped and the reactor connected to a vacuum (1–2 Torr) and the deposit allowed to dry until all chloroform was removed. After evaporation of the solvent iomeprol solution with iodine concentration of 260 g/l was added at 60° C. to the reactor. The expanded three dimensional lipid deposit was allowed to hydrate for 30 minutes. The liposomes suspension was extruded at 60° C. through a 2 μm polycarbonate membrane (Nuclepore) and after cooling to room temperature it was concentrated to 30 g lipids/l. The entrapped iodine to lipid ratio (I/L) was above 4.0.

The same experiment was then repeated with reticulated carbon, reticulated nickel and reticulated glassy carbon as the column packing. Bulk densities of the three dimensional lipid structure obtained in these experiments were between 0.05 and 0.005 g/cm$^3$. Liposomes with lipid to iodine ratio of 3.5–4.5 were obtained.

EXAMPLE 5

A glass column (500 mm high and 50 mm in diameter) filled with hollow glass beads as an array of inert packing and operated as a fluidized bed reactor. A lipid solution containing 50 g/l of a mixture of dipalmitoylphosphatidylcholine (DPPC), cholesterol and dipalmitoylphosphatidic acid (DPPA) with molar ratio 5:4:1 in cyclohexane/ethanol azeotropic mixture (69.5/30.5 v/v) was introduced into the column containing a 100 mm high bed of hollow glass spheres supported by a porous glass frit. The solution was allowed to thoroughly wet the glass beads and the excess removed. A stream of hot (80° C.) air was blown from the bottom through the reactor and the spheres were fluidized until the lipid deposit was almost dry. The air flow was then stopped, the reactor connected to a vacuum (1–2 Torr) and the deposit allowed to dry until complete removal of solvents. After evaporation of the solvent, a 4% by weight lidocaine HCl solution in water (pH 7.2) at 60° C. was added to the reactor. The liposome solution formed was extruded at 80° C. through a 2 μm polycarbonate membrane (Nuclepore) and after cooling to room temperature concentrated to 35 mg lipid/ml. The entrapped lidocaine in liposomes was 0.35 mmol lidocaine/g lipid.

Various expansions (20–80%) of the bed during the fluidization showed little influence on the quality of the deposit.

EXAMPLE 6

The Example 4 was repeated using a 500 mm high glass column without inert packing. The column was filled with 100 ml of lipid solution (80 g/l) prepared from azeotropic mixtures of ethanol/cyclohexane, chloroform/methanol and iso-propanol/hexane. The organic solvent was first evaporated at 55° C. and 300 mmHg of pressure and then 70° C. and 10 mmHg until formation of a foamed dry deposit. In all cases the three dimensional expanded lipid structure obtained was then hydrated at 70° C. with an aqueous solution of iomeprol to produce liposome encapsulated iomeprol suspensions. After extrusion at 70° C. on a 0.6 μm polycarbonate membrane (Nuclepore) the liposome suspension was concentrated. Typical iodine to lipid ratios (I/L) for a number of experiments run under different experimental conditions were in the range 1.9–2.5 with lipid concentrations between 25 and 35 mg/ml. Bulk densities of the expanded lipid structure were estimated to be between 0.05 and 0.001 g/cm$^3$.

We claim:

1. A method of making a suspension of liposome vesicles with enhanced entrapment capacity, said method comprising the steps of:

(a) dissolving one or more film forming lipids in at least one organic solvent to form a solution in a reaction vessel, (b) evaporating the solvent to form a thick, viscous solution, (c) subjecting the reaction vessel to reduced pressure and expanding the thickened solution into a foam, thereby producing a dry expanded three dimensional lipid structure with a bulk density below 0.1 g/cm$^3$, (d) contacting the three dimensional lipid structure with an aqueous solution carrier phase thereby producing a suspension of liposome vesicles entrapping the carrier solution.

2. The method of claim 1, wherein the bulk density of the dry expanded lipid structure is between 0.08 and 0.001 g/cm$^3$.

3. The method of claim 1, wherein the reaction vessel contains a network of inert porous packing material on which the lipids are supported or deposited.

4. The method of claim 1, wherein the dry expanded three dimensional lipid structure has a surface to volume ratio between 10 and 50,000 cm$^{-1}$.

5. The method of claim 1, wherein in step (c) the pressure in the reaction vessel is reduced to 1–2 Torr.

6. The method of claim 3, wherein the packing is selected from the group consisting of reticulated carbon, reticulated vitreous carbon, reticulated metal, glass, wool, metal wool, glass fiber or metal fiber.

7. The method of claim 3 wherein the reaction vessel is a fluidized bed reactor and the inert porous packing is hollow glass spheres.

8. The method of claim 3, wherein the reaction vessel is a column packed with Raschig rings and the lipid solution trickled down through the packed column.

9. The method of claim 1, wherein after evaporation of the organic solvent in step (b) the lipid deposit is contacted with the aqueous carrier phase which is introduced at the lower end of the column.

10. The method of claim 1, wherein the evaporation in step (b) is carried out at above ambient temperature or under vacuum.

11. The method of claim 1 or 3, wherein the solvent is evaporated in step (b) by blowing air or an inert gas through the reaction vessel.

12. The method of claim 11, wherein nitrogen is blown through the reaction vessel.

13. The method of claim 1 or 3, wherein the organic solvent is selected from the group consisting of chloroform, petroleum ether, methanol, ethanol, propanol, iso-propanol, n-butanol, tert-butanol, pentanol, hexanol, pentane, hexane, heptane, cyclohexane and mixtures thereof.

14. The method of claim 13, wherein the organic solvent is an azeotropic mixture of two solvents.

15. The method of claim 14, wherein the solvent is a mixture of ethanol and cyclohexane, chloroform and methanol, or isopropanol and hexane.

16. The method of claim 1, wherein the aqueous carrier phase contains a biologically active substance.

17. The method of claim 16, wherein the active substance is a contrast agent.

18. The method of claim 17, wherein the contrast agent is an iodinated X-ray contrast agent.

19. The method of claim 18, wherein the iodine to lipid ratio of the liposomes vesicles is at least 2.75.

* * * * *